(12) United States Patent
Son et al.

(10) Patent No.: US 9,195,948 B2
(45) Date of Patent: Nov. 24, 2015

(54) CLINICAL DIAGNOSIS SUPPORT METHOD AND SYSTEM BASED ON HIERARCHICAL FUZZY INFERENCE TECHNOLOGY

(75) Inventors: Chang Sik Son, Daegu-si (KR); Yoon Nyun Kim, Daegu-si (KR); Hee Joon Park, Daegu-si (KR); Suk Tae Seo, Ulsan-si (KR); Min Soo Kim, Daegu-si (KR)

(73) Assignee: KEIMYUNG UNIVERSITY INDUSTRY ACADEMIC COOPERATION FOUNDATION, Daegu-Si (KR)

( * ) Notice: Subject to any disclaimer, the term of this patent is extended or adjusted under 35 U.S.C. 154(b) by 270 days.

(21) Appl. No.: 13/988,346

(22) PCT Filed: Aug. 1, 2011

(86) PCT No.: PCT/KR2011/005664
§ 371 (c)(1),
(2), (4) Date: May 20, 2013

(87) PCT Pub. No.: WO2012/102444
PCT Pub. Date: Aug. 2, 2012

(65) Prior Publication Data
US 2013/0246330 A1 Sep. 19, 2013

(30) Foreign Application Priority Data
Jan. 26, 2011 (KR) ........................ 10-2011-0007873

(51) Int. Cl.
| | |
|---|---|
| *G06F 15/18* | (2006.01) |
| *G06N 7/02* | (2006.01) |
| *G06F 19/00* | (2011.01) |
| *G06N 5/04* | (2006.01) |
| *G06Q 50/22* | (2012.01) |

(52) U.S. Cl.
CPC ............... *G06N 7/02* (2013.01); *G06F 19/345* (2013.01); *G06N 5/048* (2013.01); *G06Q 50/22* (2013.01)

(58) Field of Classification Search
CPC ....................................................... G06N 7/02
See application file for complete search history.

(56) References Cited

U.S. PATENT DOCUMENTS

| | | | |
|---|---|---|---|
| 5,577,169 A | 11/1996 | Prezioso | |
| 5,819,242 A * | 10/1998 | Matsuoka et al. ................ | 706/2 |
| 2007/0149862 A1* | 6/2007 | Pipke ............................ | 600/301 |
| 2008/0281170 A1* | 11/2008 | Eshelman et al. ............ | 600/301 |
| 2009/0248450 A1* | 10/2009 | Fernandez ....................... | 705/3 |
| 2011/0119212 A1* | 5/2011 | De Bruin et al. ............... | 706/12 |
| 2012/0053073 A1* | 3/2012 | Kassis .............................. | 506/9 |
| 2013/0289364 A1* | 10/2013 | Colman et al. ................ | 600/301 |

FOREIGN PATENT DOCUMENTS

| | | |
|---|---|---|
| JP | 05-289880 A | 11/1993 |
| JP | 06-102907 A | 4/1994 |
| JP | 07-134651 A | 5/1995 |
| JP | 07-302202 A | 11/1995 |

* cited by examiner

*Primary Examiner* — Alan Chen
(74) *Attorney, Agent, or Firm* — Revolution IP, PLLC (57) ABSTRACT

Disclosed is a clinical diagnosis supporting method and system based on hierarchical fuzzy inference. The clinical diagnosis supporting method includes the steps of: (a) extracting check data of a plurality of check items for each of a plurality of patients from a respective check item database; (b) selecting a characteristic from the check data of each of the check items; (c) hierarchical fuzzy-inferring the check data from which the characteristic is selected, for each check item; (d) extracting a check opinion for each disease based on an output value of the fuzzy inference for each check item; and (e) making a synthetic clinical estimation based on the extracted check opinion.

21 Claims, 5 Drawing Sheets

FIG. 7

CLINICAL DIAGNOSIS SUPPORT METHOD AND SYSTEM BASED ON HIERARCHICAL FUZZY INFERENCE TECHNOLOGY

CROSS REFERENCE TO PRIOR APPLICATIONS

This application is a National Stage Application of PCT International Patent Application No. PCT/KR2011/005664 filed on Aug. 1, 2011, under 35 U.S.C. §371, which claims priority to Korean Patent Application No. 10-2011-0007873 filed on Jan. 26, 2011, which are all hereby incorporated by reference in their entirety.

BACKGROUND OF THE INVENTION

1. Field of the Invention

The present invention relates to a clinical diagnosis support method and system, and more particularly, to a clinical diagnosis support method and system based on a fuzzy inference technology for minimizing the number of patterns of error classification in an intermediate layer to improve classification capability of hierarchical fuzzy inference.

2. Description of the Related Art

In general, the design of a fuzzy system has a close connection with time-consuming activity related to generation of knowledge, reduction in the total number of rules and variation of relevant parameters, all of which have an effect on precision and understanding power of the fuzzy system.

In recent years, various approaches to automatically generate fuzzy rules from training (or learning) data have been proposed, including heuristic approach, neuro-fuzzy approach, genetic approach, hierarchical approach to overcome a 'curse of dimensionality' problem.

Most of standard fuzzy systems (SFs) have a problem that increase in the number of input variables (i.e., dimensions) may lead to exponential increase in the number of possible candidate fuzzy rules, which requires an additional learning techniques such as a neural network and a genetic algorithm and consumes a long time to construct a knowledge database for classification or inference.

Various relevant studies including approximation capability of nonlinear functions in a hierarchical fuzzy system have been made. The hierarchical fuzzy system brings results ensuring usefulness in overcoming a problem of explosive amount of computation of standard fuzzy systems and also includes advanced approaches to optimize parameters in nonlinear processes.

However, the main problem of the hierarchical fuzzy system is that results in an intermediate layer contain physical meanings when results in a previous layer and input values in a subsequent layer are mapped as variables for the following layers. Therefore, there is a need to describe a rule-based appearance to reduce the number of rules related to an intermediate layer in the hierarchical fuzzy system in order to alleviate such a main problem.

SUMMARY OF THE INVENTION

To overcome the above problems, it is an object of the invention to provide a schema of a hierarchical fuzzy classification system based on statistical characteristics.

It is another object of the invention to provide a method and system for minimize the number of patterns of error classification in an intermediate layer to improve classification capability of a hierarchical fuzzy classification system.

To achieve the above objects, according to a first aspect of the invention, there is provided a clinical diagnosis supporting method based on hierarchical fuzzy inference, including the steps of: (a) extracting check data of a plurality of check items for each of a plurality of patients from a respective check item database; (b) selecting a characteristic from the check data of each of the check items; (c) hierarchical fuzzy-inferring the check data from which the characteristic is selected, for each check item; (d) extracting a check opinion for each disease based on an output value of the fuzzy inference for each check item; and (e) making a synthetic clinical estimation based on the extracted check opinion.

Preferably, the check items include a blood check, a urine check and radiation check, and the step (b) includes: marking each check data with a result of clinical diagnosis; and calculating a cut-off value for determination of clinical diagnosis for each check item.

Preferably, the step (c) has a hierarchical input/output structure of a plurality of fuzzy systems where an output value is generated with an output of one fuzzy system having a check data of each check item as an input and with another check data as an input, and the number of inputs of the fuzzy system is at least 3.

Preferably, the step (c) includes: in each fuzzy system, fuzzy-partitioning check data of each check item; and generating clinical diagnosis knowledge from the partitioned check data, and the fuzzy partitioning is divided into a normal group and an abnormal group based on a statistical distribution of the check data.

Preferably, the generation of clinical diagnosis knowledge includes the steps of: generating primary clinical diagnosis knowledge from the divided check data; and generating secondary clinical diagnosis knowledge applied to each hierarchical fuzzy system by applying an algorithm to avoid collision between the primary clinical diagnosis knowledge.

Preferably, the step (e) includes: extracting clinical characteristics and criterions presented in each inference layer; extracting an abnormal case from data of each inference layer; and making synthetic clinical inference based on the clinical characteristics and criterions and the abnormal case.

According to a second aspect of the invention, there is provided a clinical diagnosis supporting system using hierarchical fuzzy inference to perform the described method, including: a check database storing at least one check data for one or more check items; a pre-processing unit which selects characteristic data for each check item from the database; a fuzzy inference unit which performs hierarchical fuzzy inference with the characteristic data for each check item as an input; and a synthetic estimation unit which makes a synthetic clinical estimation based on a check opinion for each check item, which is extracted through the fuzzy inference.

Preferably, the synthetic estimation unit provides clinical characteristics and criterions based on output values of each inference layer, and an abnormal case is extracted based on output values of each inference layer.

According to the present invention, there is provided a method for detecting a condition of an emergency patient to infer his/her disease by providing results of hierarchical and synthetic clinical inference using the hierarchical fuzzy inference technique. In addition, the inference results can be provided based on information on all knowledge accumulated in the hospital information system for several years or several decades, which may result in increased precision of diagnosis.

In addition, based on clinical information (blood, urine, radiation) of patients and results of hierarchical and synthetic inference, main parameters, clinical criterions and optimized knowledge for differential diagnosis for each disease can be provided to infer a possible disease of an emergency patient and assist in discipline of medical workers including medical students.

DETAILED DESCRIPTION OF PREFERRED EMBODIMENTS

Hereinafter, preferred embodiments of the present invention will be described in detail with reference to the accompanying drawings.

Figure 1:
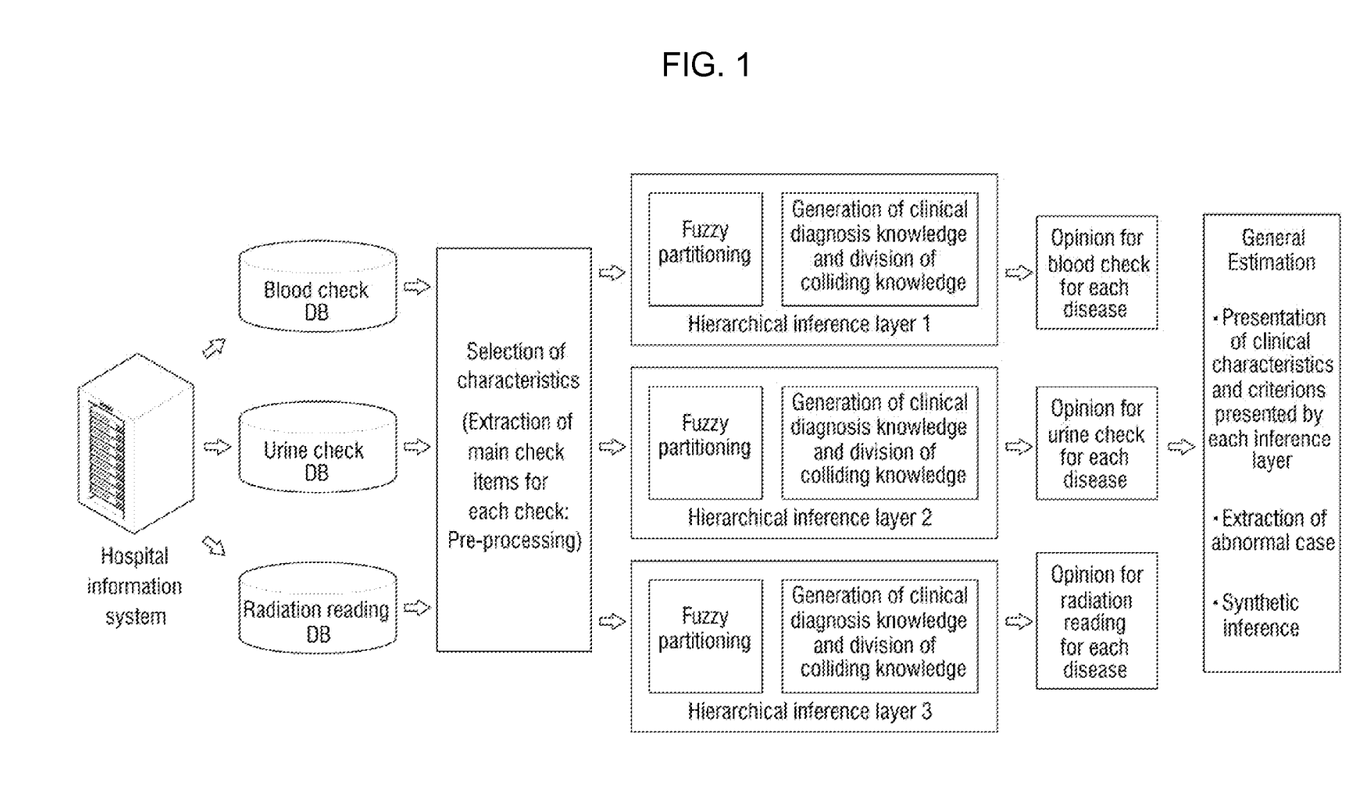
FIG. 1 is a flow diagram showing a clinical diagnosis supporting method based on hierarchical fuzzy inference according to an embodiment of the present invention.

FIG. 1 is a flow diagram showing a clinical diagnosis supporting method based on hierarchical fuzzy inference according to an embodiment of the present invention. As shown in FIG. 1, a clinical diagnosis supporting method of this invention includes the steps of: (a) extracting check data of a plurality of check items for each of a plurality of patients from a respective check item database; (b) selecting a characteristic from the check data of each of the check items; (c) hierarchical fuzzy-inferring the check data from which the characteristic is selected, for each check item; (d) extracting a check opinion for each disease based on an output value of the fuzzy inference for each check item; and (e) making a synthetic clinical estimation based on the extracted check opinion.

As another aspect of the invention, a clinical diagnosis supporting system includes a check database storing at least one check data for one or more check items; a pre-processing unit which selects characteristic data for each check item from the database; a fuzzy inference unit which performs hierarchical fuzzy inference with the characteristic data for each check item as an input; and a synthetic estimation unit which makes a synthetic clinical estimation based on a check opinion for each check item, which is extracted through the fuzzy inference.

In the step (a), input data consist of check data of a plurality of patients which consist of a plurality of check items, and include determined clinical diagnosis information for each patient.

The check data of the plurality of patients are classified and arranged for each check item through the check database of a hospital information system, each check data is marked with a result of clinical diagnosis, and a characteristic is selected.

A method of selecting a characteristic will be described in more detail below. First, the check data of the plurality of patients are classified and arranged for each check item. For example, (I) a urine check item includes many check items such as color, a level of albumin, the number of white blood cells, the number of red blood cells, etc., (II) a blood check item includes total blood cell check item (the number of white blood cells, the number of red blood cells, a level of hemoglobin, etc.), arterial blood gas check item (levels of sodium, potassium, amylase, etc.), basic check items for inpatients (levels of calcium, glucose, cholesterol, etc.) and so on, (III) a radiation check opinion item includes important leading parameters for disease diagnosis for each clinical department such as chest X-ray, CT, MRI, etc.

As described above, when the check data of the plurality of check items for each of the plurality of patients are received and classified for each check item and are arranged according to a magnitude of value and results of clinical diagnosis are marked with each check data, a region in which the results of clinical diagnosis overlap appears.

The clinical supporting system estimates a goodness-of-fit for determination of the clinical diagnosis based on the overlapping region. That is, a degree of separability to indicate a degree of separation of the plurality of check data included in the overlapping region for each result of clinical diagnosis is calculated, the sum of degrees of separability is calculated, and a goodness-of-fit to indicate a degree of suitability of the check item for the check data for determination of the clinical diagnosis is determined.

Through this process, a goodness-of-fit for determination of clinical diagnosis for all check items is calculated and a rank of check item for the determination of clinical diagnosis may be determined based on the calculated goodness-of-fit. Once the goodness-of-fit for each check item is determined, the clinical supporting system calculates a cut-off value to determine a result of clinical diagnosis for each check item. The cut-off value refers to an average of weights of values of check data in the overlapping region.

As described above, when the goodness-of-fit for each check item and the cut-off value for each check item are determined, a characteristic or a pattern of rules for determination of clinical diagnosis through the check items may be generated. This corresponds to the step (b) of selecting a characteristic, which is also called a pre-processing step.

Here, a degree of redundancy of the overlapping region is calculated according to the following Equation 1 and a characteristic is selected based on the calculated degree of redundancy.

$$N_j = \sum_{x_1 \in C_k} h(x_{ij})/s, \; x_{ij} \in a_j, \; j = 1, \ldots, n \quad \text{[Equation 1]}$$

In Equation 1, $h(x_{ij})$ indicates the frequency of unique attribute values included in a j-th class (normal group or abnormal group) in an i-th attribute, and s indicates the total number of attribute values. $N_j$ indicates a relative degree of separability of attribute values in the overlapping region and has values of $N_j \in [0, 1]$.

Figure 2:
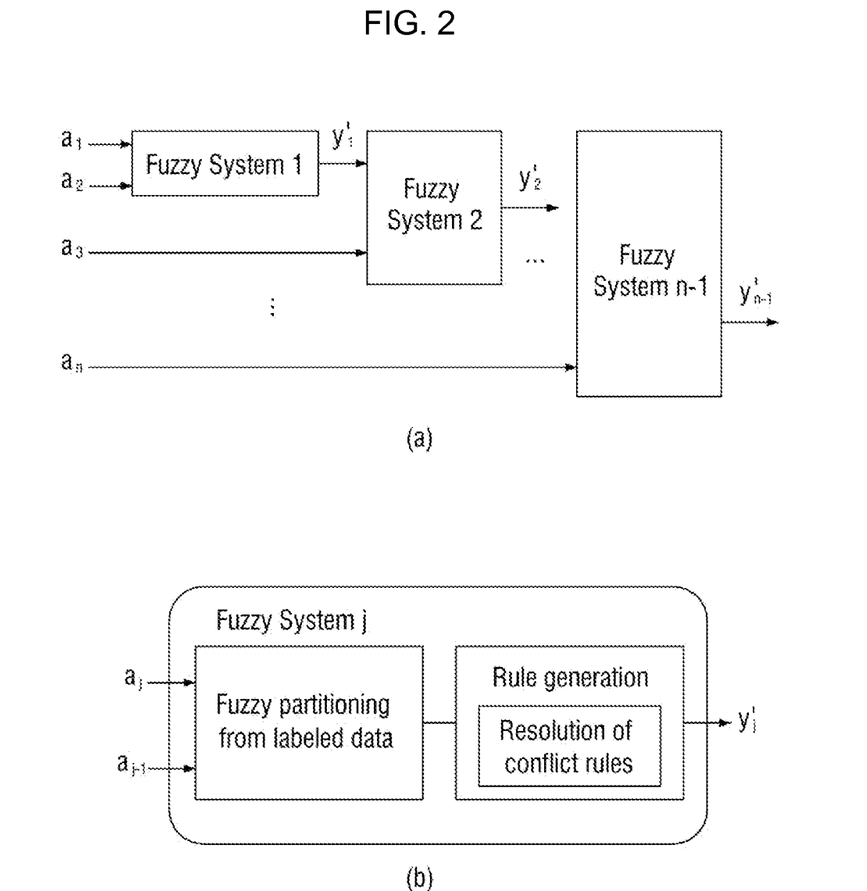
FIG. 2 is a block diagram showing a hierarchical fuzzy system applied to the clinical diagnosis supporting method according to an embodiment of the present invention.

In this manner, after a characteristic is selected from the check data for each check item in the step (b), hierarchical fuzzy inference is made in the step (c) for the check data from which the characteristic is selected for each check item. FIG. 2 is a block diagram showing a hierarchical fuzzy system applied to the clinical diagnosis supporting method according to an embodiment of the present invention. FIG. 2(*a*) shows a structure of an n-input hierarchical fuzzy inference system (HFCS) and FIG. 2(b) shows a substructure of a j-th fuzzy system in the hierarchical fuzzy system (HFCS).

As shown in FIG. 2, a1, a2, a3, ..., $a_n$ are input variables including a urine check item, a blood check item, a radiation check opinion item, etc.

As described above, (I) the urine check item includes many check items such as color, a level of albumin, the number of white blood cells, the number of red blood cells, etc., (II) the blood check item includes total blood cell check item (the number of white blood cells, the number of red blood cells, a level of hemoglobin, etc.), arterial blood gas check item (levels of sodium, potassium, amylase, etc.), basic check items for inpatients (levels of calcium, glucose, cholesterol, etc.) and so on, (III) the radiation check opinion item includes important leading parameters for disease diagnosis for each clinical department such as chest X-ray, CT, MRI, etc. Check results and opinions of these three main check items (urine, blood and radiation) correspond to input values of the hierarchical fuzzy inference system of this invention.

In FIG. 2, y1, y2, ..., $y_{n-1}$ are output values of each layer. For example, if hierarchical inference is performed with only four urine check items (color, a level of albumin, the number of white blood cells, and the number of red blood cells), $a_1$, $a_2$, $a_3$ and $a_4$ may be defined as the number of white blood cells, the number of red blood cells, color and a level of albumin, respectively, and $y_1$ and $y_2$ indicate a result value inferred from the number of white blood cells and the number of red blood cells and a result value inferred from the result value of $y_1$ and the level of albumin, respectively. Accordingly, a final output value $y_3$ may be assumed as a synthetic inference result of these four check items (color, a level of albumin, the number of white blood cells, and the number of red blood cells).

In this manner, the hierarchical fuzzy inference system of this invention continues to generate fuzzy systems with an output of one fuzzy system having a check data of each check item as an input and with another check data as a new input, and has an output value which corresponds to a synthetic value of all inputs.

As shown in FIG. 2, the step of hierarchical fuzzy inference has a hierarchical input/output structure of a plurality of fuzzy systems where an output value is generated with an output of one fuzzy system having a check data of each check item as an input and with another check data as an input. The number of inputs of the fuzzy system is preferably at least 3.

In other words, unlike conventional methods where a result of inference is provided step by step through a case of keyword-mapping from input information and the established clinical database, this invention has no problem of keyword search or mapping (an inference result for disease, diagnosis information and treatment cannot be provided in the absence of a case corresponding to a hospital clinical database) and is capable of stepwise approximate inference since clinical knowledge is automatically configured from RAW data for each disease (basic clinical check—results of reading of urine, blood and radiation check, etc.) of the hospital clinical database.

As shown in FIG. 2, the step (c) includes the step of: in each fuzzy system, fuzzy-partitioning check data of each check item; and generating clinical diagnosis knowledge from the partitioned check data.

Figure 3:
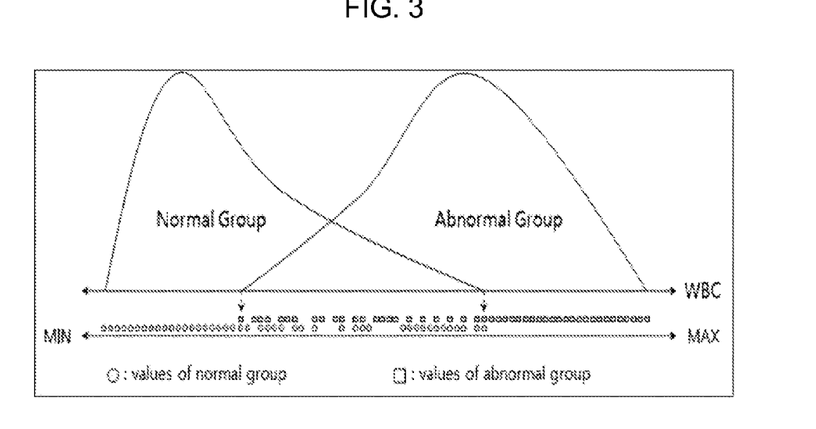
FIG. 3 is a graph showing an example of a data distribution of a normal group and an abnormal group in input variable white blood cell (WBC).

FIG. 3 is a graph showing an example of a data distribution of a normal group and an abnormal group in input variable white blood cell (WBC). In FIG. 3, MIN and MAX indicate the minimal value and the maximal value of the input variable WBC. A domain of this variable may be expressed as $D_j = [\min(a_j), \max(a_j)]$.

A step of finding this domain is a first step of fuzzy partitioning where an internal interval of data attribute values is extracted. Here, a domain $D_j = [\min(a_j), \max(a_j)]$ of a j-th attribute $a_j$ and internal intervals $I_{jk} \in c_k$ of values of the j-th attribute corresponding to any class are extracted.

A second step of fuzzy partitioning is to detect an overlapping region between the extracted internal intervals. An overlapping region $O_j = [O_j^{Lj}, O_j^{Uj}]$ between the extracted internal intervals indicates the lower and upper bounds between all overlapping regions.

Finally, input variable WBC fuzzy partitioning is expressed by the following Equation 2.

$$P_j = \text{round}(\{\max(a_j) - \min(a_j)\}/\alpha \cdot \sigma_j) \quad [\text{Equation 2}]$$

Where, partitioning $P_j$ of a j-th input variable (i.e., white blood cell item) is the number of fuzzy partitioning which is determined by a division of a difference between the maximal value and minimal value of a white blood domain by $\alpha \times \sigma_j$ ($\alpha > 0$). In other words, this means that the standard deviation $\sigma_j$ for the entire data of the white blood cell item determines the number of fuzzy partitioning of the white blood cell item based on a value of variable $\alpha$.

$$W_j = (o_j^{Uj} - o_j^{Lj})/(P_j - 1) \quad [\text{Equation 3}]$$

Figure 4:
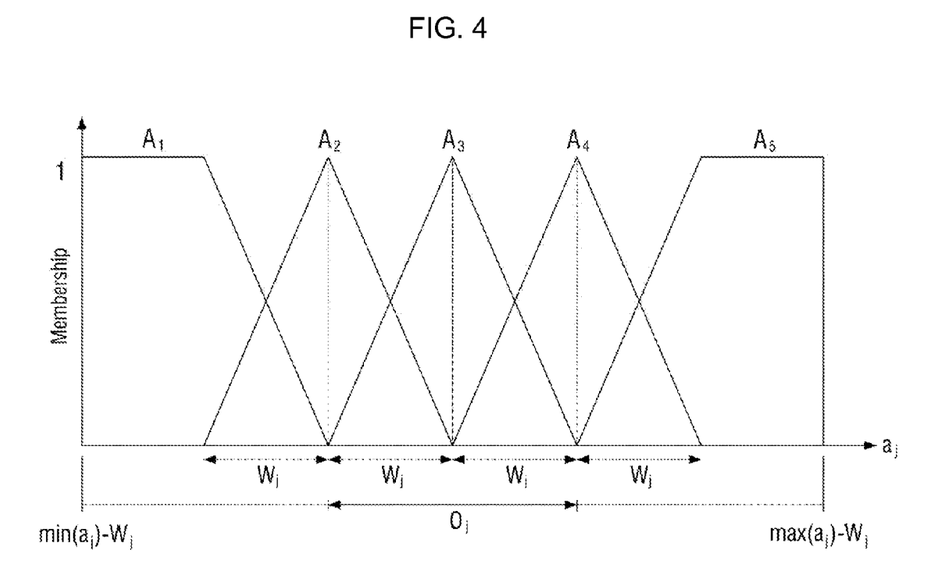
FIG. 4 is a view showing an example of fuzzy partitioning of white blood cell check items with a method of the present invention.

Fuzzy partitioning as shown in FIG. 4 can be achieved using the number of partitioning $P_j$ of the white blood cell item determined in Equation 1 and the lower bound $o_j^{Lj}$ and the upper bound $o_j^{Uj}$ of the overlapping region determined in Equation 3. FIG. 4 is a view showing an example of fuzzy partitioning of the white blood cell check item with a method of the present invention.

Figure 5:
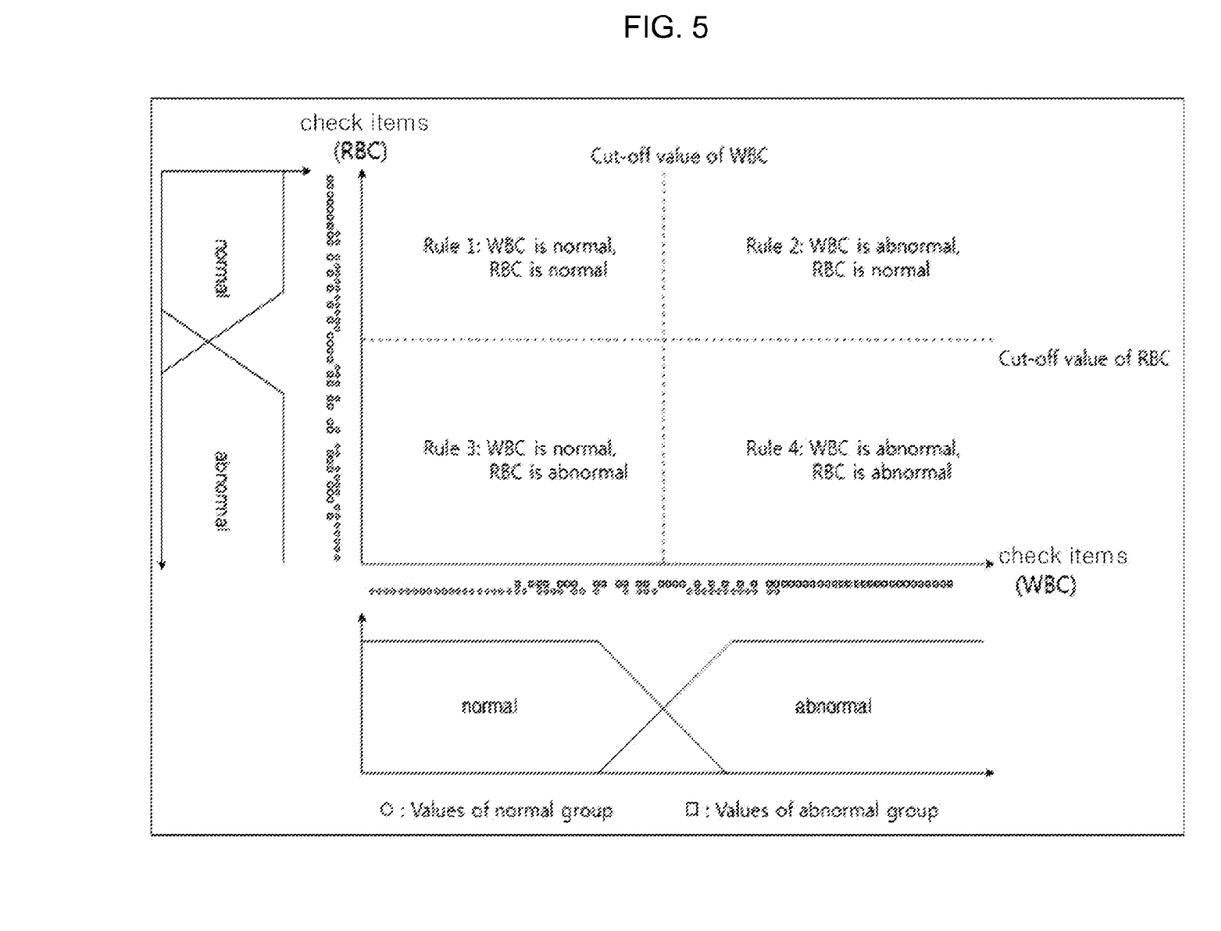
FIG. 5 is a view showing an example of input variable white blood cell and red blood cell two-variable fuzzy partitioning with a method of the present invention.

A second step of fuzzy inference is to generate new clinical diagnosis (rule generation) based on the above fuzzy partitioning. FIG. 5 is a view showing an example of input variable white blood cell and red blood cell fuzzy partitioning with a method of the present invention.

As shown in FIG. 5, a format of Rule 1: "WBC is normal, RBC is normal" corresponds to a condition of $R_k^1$: If $a_1$ is $A_{k,1}$ and $a_2$ is $A_{k,2}$ Then $y_1$ is $c_k$. It is assumed that the following candidate rule patterns are generated with input of numeral value data of the normal group and the abnormal group.

$$\mu_k'(x_i) = \mu_{k,1}(x_{i1}) \times \mu_{k,2}(x_{i2}) \quad [\text{Equation 4}]$$

$$\mu_k'(x_i) = \max_k \{\mu_k'(x_i) : k = 1, \ldots, m\} \quad [\text{Equation 5}]$$

<Normal Group>
R1: If WBC is normal and RBC is normal Then output is normal {0.90, sup=20}
R2: If WBC is normal and RBC is abnormal Then output is normal {0.8, sup=10}
<Abnormal Group>
R3: If WBC is abnormal and RBC is abnormal Then output is abnormal {1.0, sup=15}
R4: If WBC is abnormal and RBC is normal Then output is abnormal {0.6, 7}
R5: If WBC is normal and RBC is abnormal Then output is abnormal {0.8, sup=3}

In the above rule patterns, {A, B} means the frequency (B) of rules corresponding to the maximum goodness-of-fit (calculated from Equation 4 and Equation 5), and the knowledge R2 of the normal group collides with the knowledge R5 of the abnormal group. In this invention, Table 1 is used to overcome this collision. Table 1 shows a collision rule solution strategy applied to this invention.

TABLE 1

| Frequency | Maximum degree | | |
|---|---|---|---|
| | $\gamma > \delta$ | $\gamma = \delta$ | $\gamma < \delta$ |
| $\alpha > \beta$ | $c_p$ | $c_p$ | $c_p$ |
| $\alpha = \beta$ | $c_p$ | NA | $c_q$ |
| $\alpha < \beta$ | $c_q$ | $c_q$ | $c_q$ |

In case of collision rule between two different groups in Table 1, the knowledge R2 of the normal group is determined as the candidate rule pattern, "If WBC is normal and RBC is abnormal Then output is normal {0.8, sup=10}" since a condition of $\alpha > \beta$ in the frequency is satisfied for the maximum goodness-of-fit.

In this manner, candidate rules of Fuzzy System 1, Fuzzy System 2, ..., Fuzzy System n−1 are generated in FIG. 2. However, the rules from Fuzzy System 2 to Fuzzy System n−1 are generated using outputs of the previous step (that is, a result of inference of Fuzzy System 1 for Fuzzy System 2) and inference is made in comprehensive consideration of all input values, which may result in low rate of misdiagnosis.

In this embodiment, fuzzy partitioning of the next layer is re-adjusted according to two steps.

Figure 6:
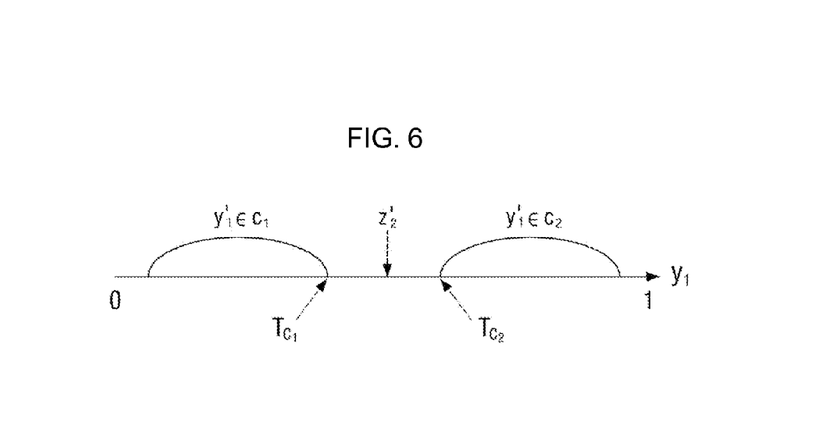
FIG. 6 is a view showing an example of fuzzy partitioning of input variables of the next layer using results of fuzzy inference of the previous layer with a method applied to the present invention.

FIG. 6 is a view showing an example of fuzzy partitioning of input variables of the next layer using results of fuzzy inference of the previous layer with a method applied to the present invention. As shown in FIG. 6, a first step of fuzzy partitioning is to find a boundary point of fuzzy partitioning from a result of fuzzy inference of the previous layer.

Here, $\tau_j$ is a standard deviation of results obtained from the following Equation 6.

$$y_j^* = \sum_{y_j} y_j \cdot \mu_k(y_j) \bigg/ \sum_{y_j} \mu_k(y_j), \; j = 1, \ldots, n-1 \quad \text{[Equation 6]}$$

where $\mu_k(y_j) = \max_k [\mu_k^j(x_i) \times \mu_k(y_j)]$

Figure 7:
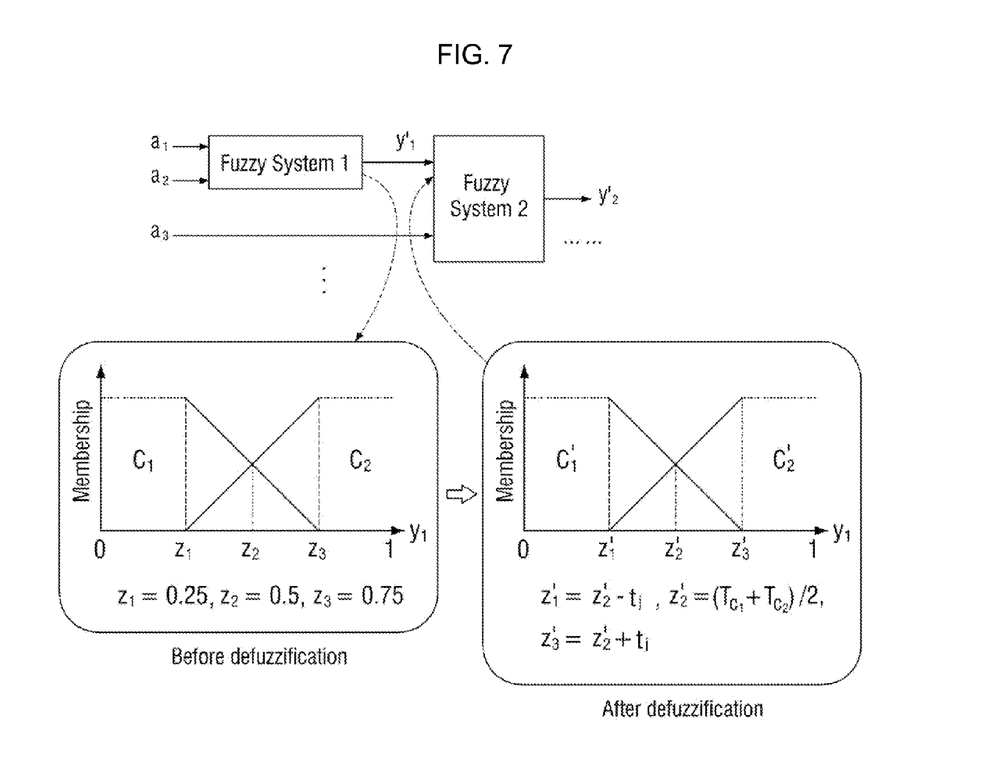
FIG. 7 is a schematic view showing a fuzzy function generated from the results of fuzzy inference of the previous layer applied to the present invention.

FIG. 7 is a schematic view showing a fuzzy function generated from the results of fuzzy inference of the previous layer applied to the present invention. As shown in FIG. 7, a second step is to generate a new fuzzy function based on a boundary point found in the first step.

In this manner, in this invention, a parameter of a fuzzy function is re-adjusted from the results of fuzzy inference of the previous layer, which is repeated until all input values applied to the hierarchical fuzzy inference system (HFCS) of this invention are exhausted.

Results of Experiment

An experiment on the conventional three types of classification methods (statistical classifiers, SVMs with three kernel functions, and fuzzy rule learning methods with rules weights) and the suggested method was made with well known five data sets (Haverman' survival, Blood transfusion service center, New thyroid disease, Pima Indians diabetes, and Wisconsin breast cancer original).

Main characteristics of these data sets are listed in Table 2. Each data set is randomly divided into 10 groups and samples of each item are constantly specified in each group. Input combinations of 10-fold CV (Cross validation) and the suggested HFCS are determined based on the degree of redundancy calculated by Equation 1.

TABLE 2

| Dataset | No. of sample | No. of input feature | No. of class |
|---|---|---|---|
| Hab. | 306 | 3 | 2 |
| Blood | 748 | 4 | 2 |
| NT | 215 | 5 | 3 |
| PID | 768 | 8 | 2 |
| WBCO | 683 | 9 | 2 |

The following Table 3 and Table 4 show an average classification correction rate experimented during 10-fold CV (Cross Validation).

TABLE 3

| | Statistical classifiers*(%) | | | SVMs*(%) | | |
|---|---|---|---|---|---|---|
| Dataset | LDA | QDA | kNN | Poly. | RBF | Sig. |
| Hab. | 74.82 | 75.13 | 66.97 | 26.47 | 70.61 | 73.53 |
| Blood | 76.74 | 38.10 | 64.45 | 23.79 | 74.60 | 76.21 |
| NT | 91.26 | 96.75 | 97.21 | 13.96 | 70.74 | 69.81 |
| PID | 77.10 | 74.38 | 70.33 | 65.11 | 65.11 | 65.11 |
| WBCO | 96.05 | 95.02 | 96.05 | 93.71 | 89.46 | 65.01 |
| Avg. ± Sd | 83.19 ± 9.74 | 75.88 ± 23.62 | 79.00 ± 16.23 | 44.61 ± 33.66 | 74.10 ± 9.23 | 69.93 ± 5.00 |

TABLE 4

| | Fuzzy rule learning methods*(%) | | | | |
|---|---|---|---|---|---|
| Dataset | Chi_RW | Ishibuchi99 | Fuzzy slave | Shi et al. | HFCS (%) |
| Hab. | (P = 2) 73.53, (P = 3) 73.19, (P = 4) 71.23 | (P = 2) 73.53, (P = 3) 73.20, (P = 4) 73.20 | (P = 2) 73.20, (P = 3) 74.49, (P = 4) 71.55 | (P = 2) 71.23, (P = 3) 71.56, (P = 4) 74.12 | $\alpha = 1.27, 77.74$ ($L_1$: 17.4, $L_2$: 5.9) |

TABLE 4-continued

| Dataset | Fuzzy rule learning methods*(%) | | | | |
|---|---|---|---|---|---|
| | Chi_RW | Ishibuchi99 | Fuzzy slave | Shi et al. | HFCS (%) |
| Blood | (P = 2) 76.07, | (P = 2) 76.21, | (P = 2) 76.47, | (P = 2) 76.74, | $\alpha$ = 1.62, 76.20 |
| | (P = 3) 76.61, | (P = 3) 76.07, | (P = 3) 75.81, | (P = 3) 75.54, | ($L_1$: 22.5, $L_2$: 8.2, $L_3$: 4.0) |
| | (P = 4) 76.87 | (P = 4) 76.21 | (P = 4) 76.47 | (P = 4) 75.94 | |
| NT | (P = 2) 84.24, | (P = 2) 78.61, | (P = 2) 94.46, | (P = 2) 84.26, | $\alpha$ = 0.9, 93.03, |
| | (P = 3) 78.16, | (P = 3) 75.84, | (P = 3) 88.94, | (P = 3) 86.97, | ($L_1$: 35.4, $L_2$: 17.2, $L_3$: 19.9, |
| | (P = 4) 89.85 | (P = 4) 69.81 | (P = 4) 79.57 | (P = 4) 85.11 | $L_4$: 18.2) |
| PID | (P = 2) 65.76, | (P = 2) 65.11, | (P = 2) 76.71, | (P = 2) 72.78, | $\alpha$ = 1.3, 75.01, |
| | (P = 3) 72.40, | (P = 3) 64.98, | (P = 3) 74.36, | (P = 3) 71.87, | ($L_1$: 17.5, $L_2$: 8.7, L4: 10.5, |
| | (P = 4) 73.44 | (P = 4) 68.24 | (P = 4) 72.14 | (P = 4) 72.50 | $L_4$: 12.4, $L_5$: 11.1, $L_6$: 9.4, $L_7$: 8.6) |
| WBCO | (P = 2) 94.29, | (P = 2) 95.17, | (P = 2) 96.50, | (P = 2) 94.58, | $\alpha$ = 1.2, 95.76, |
| | (P = 3) 91.21, | (P = 3) 96.34, | (P = 3) 95.03, | (P = 3) 95.47, | ($L_1$: 8.2, $L_2$: 8.4, $L_3$: 6.0, $L_4$: 4.9, |
| | (P = 4) 73.21 | (P = 4) 95.76 | (P = 4) 96.63 | (P = 4) 93.13 | $L_5$: 6.8, $L_6$: 6.0, $L_7$: 4.6, $L_8$: 5.2) |
| Avg. ± Sd | (P = 2) 78.78 ± 10.89 | (P = 2) 77.73 ± 11.00 | (P = 2) 83.47 ± 11.08 | (P = 3) 80.28 ± 10.54 | 83.55 ± 10.00 |

In Table 3 and Table 4, parameter values of SVMs (i.e., kernel types: Polynomial, RBF, and Sigmoid functions: 1000; eps: 0.01; degree(d): 10; gamma(g): 1.0; coef0(r): 1.0; and shrinking(h): 0.0) are default values provided by KEEL Ver 1.2.

Here, 'Avg±Sd' indicates average prediction performance of each classification method for the five data sets, 'P' in Table 4 indicates the number of fuzzy partitioning, and '$L_i$' indicates the average number of rules in each layer of HFCS.

It can be seen that the classification prediction performance of HFCS of this invention suggested in Table 4 becomes maximal when the parameter a is updated to 1.27, 1.62, 0.9, 1.3 and 1.2. In addition, although the HFCS of this invention having different numbers of fuzzy partitioning is lower in classification precision that fuzzy slave (P=2) having the maximum classification prediction performance among fuzzy rule learning methods, it can be seen that the HFCS calculates better average testing prediction performance than the conventional three classification methods. These results show that the prediction performance of this invention has close relation with the number of fuzzy partitioning defined in the overlapping region.

As described above, the present invention provides a method for detecting a condition of an emergency patient to infer his/her disease by providing results of hierarchical and synthetic clinical inference using the hierarchical fuzzy inference technique. In addition, the inference results can be provided based on information on all knowledge accumulated in the hospital information system for several years or several decades, which may result in increased precision of diagnosis.

In addition, based on clinical information (blood, urine, radiation) of patients and results of hierarchical and synthetic inference, main parameters, clinical criterions and optimized knowledge for differential diagnosis for each disease can be provided to infer a possible disease of an emergency patient and assist in discipline of medical workers including medical students.

Although a few exemplary embodiments have been shown and described, it will be appreciated by those skilled in the art that adaptations and changes may be made in these exemplary embodiments without departing from the spirit and scope of the invention, the scope of which is defined in the appended claims and their equivalents.

What is claimed is:

1. A clinical diagnosis supporting method based on hierarchical fuzzy inference, comprising the steps of:
   (a) extracting check data of a plurality of check items for each of a plurality of patients from a respective check item database;
   (b) selecting a characteristic from the check data of each of the check items;
   (c) hierarchical fuzzy-inferring the check data from which the characteristic is selected, for each check item;
   (d) extracting a check opinion for each disease based on an output value of the fuzzy inference for each check item; and
   (e) making a synthetic clinical estimation based on the extracted check opinion.

2. The clinical diagnosis supporting method according to claim 1, wherein the check items include a blood check, a urine check and radiation check.

3. The clinical diagnosis supporting method according to claim 1, wherein the step (b) includes:
   marking each check data with a result of clinical diagnosis; and
   calculating a cut-off value for determination of clinical diagnosis for each check item.

4. The clinical diagnosis supporting method according to claim 1, wherein the step (c) has a hierarchical input/output structure of a plurality of fuzzy systems where an output value is generated with an output of one fuzzy system having a check data of each check item as an input and with another check data as an input, and the number of inputs of the fuzzy system is at least 3.

5. The clinical diagnosis supporting method according to claim 2, wherein the step (c) has a hierarchical input/output structure of a plurality of fuzzy systems where an output value is generated with an output of one fuzzy system having a check data of each check item as an input and with another check data as an input, and the number of inputs of the fuzzy system is at least 3.

6. The clinical diagnosis supporting method according to claim 3, wherein the step (c) has a hierarchical input/output structure of a plurality of fuzzy systems where an output value is generated with an output of one fuzzy system having a check data of each check item as an input and with another check data as an input, and the number of inputs of the fuzzy system is at least 3.

7. The clinical diagnosis supporting method according to claim 4, wherein the step (c) includes: in each fuzzy system, fuzzy-partitioning check data of each check item; and generating clinical diagnosis knowledge from the partitioned check data.

8. The clinical diagnosis supporting method according to claim 5, wherein the step (c) includes: in each fuzzy system, fuzzy-partitioning check data of each check item; and
generating clinical diagnosis knowledge from the partitioned check data.

9. The clinical diagnosis supporting method according to claim 6, wherein the step (c) includes: in each fuzzy system, fuzzy-partitioning check data of each check item; and
generating clinical diagnosis knowledge from the partitioned check data.

10. The clinical diagnosis supporting method according to claim 7, wherein the fuzzy partitioning is divided into a normal group and an abnormal group based on a statistical distribution of the check data.

11. The clinical diagnosis supporting method according to claim 8, wherein the fuzzy partitioning is divided into a normal group and an abnormal group based on a statistical distribution of the check data.

12. The clinical diagnosis supporting method according to claim 9, wherein the fuzzy partitioning is divided into a normal group and an abnormal group based on a statistical distribution of the check data.

13. The clinical diagnosis supporting method according to claim 4, wherein the generation of clinical diagnosis knowledge includes the steps of:
generating primary clinical diagnosis knowledge from the divided check data; and
generating secondary clinical diagnosis knowledge applied to each hierarchical fuzzy system by applying an algorithm to avoid collision between the primary clinical diagnosis knowledge.

14. The clinical diagnosis supporting method according to claim 5, wherein the generation of clinical diagnosis knowledge includes the steps of:
generating primary clinical diagnosis knowledge from the divided check data; and
generating secondary clinical diagnosis knowledge applied to each hierarchical fuzzy system by applying an algorithm to avoid collision between the primary clinical diagnosis knowledge.

15. The clinical diagnosis supporting method according to claim 6, wherein the generation of clinical diagnosis knowledge includes the steps of:
generating primary clinical diagnosis knowledge from the divided check data; and
generating secondary clinical diagnosis knowledge applied to each hierarchical fuzzy system by applying an algorithm to avoid collision between the primary clinical diagnosis knowledge.

16. The clinical diagnosis supporting method according to claim 13, wherein the step (e) includes:
extracting clinical characteristics and criterions presented in each inference layer;
extracting an abnormal case from data of each inference layer; and
making synthetic clinical inference based on the clinical characteristics and criterions and the abnormal case.

17. The clinical diagnosis supporting method according to claim 14, wherein the step (e) includes:
extracting clinical characteristics and criterions presented in each inference layer;
extracting an abnormal case from data of each inference layer; and
making synthetic clinical inference based on the clinical characteristics and criterions and the abnormal case.

18. The clinical diagnosis supporting method according to claim 15, wherein the step (e) includes:
extracting clinical characteristics and criterions presented in each inference layer;
extracting an abnormal case from data of each inference layer; and
making synthetic clinical inference based on the clinical characteristics and criterions and the abnormal case.

19. A clinical diagnosis supporting system using hierarchical fuzzy inference to perform a method according to claim 12, comprising:
a check database storing at least one check data for one or more check items;
a pre-processing unit which selects characteristic data for each check item from the database;
a fuzzy inference unit which performs hierarchical fuzzy inference with the characteristic data for each check item as an input; and
a synthetic estimation unit which makes a synthetic clinical estimation based on a check opinion for each check item, which is extracted through the fuzzy inference.

20. The clinical diagnosis supporting system according to claim 19, wherein the synthetic estimation unit provides clinical characteristics and criterions based on output values of each inference layer.

21. The clinical diagnosis supporting system according to claim 19, wherein an abnormal case is extracted based on output values of each inference layer.

* * * * *